United States Patent [19]

Marcus

[11] Patent Number: 5,164,588
[45] Date of Patent: Nov. 17, 1992

[54] METHOD AND APPARATUS FOR SENSING AMBIENT CONDITIONS AT LOCATIONS ALONG AN OPTICAL FIBER TRANSMISSION PATH

[75] Inventor: Michael A. Marcus, Honeoye Falls, N.Y.

[73] Assignee: Eastman Kodak Company, Rochester, N.Y.

[21] Appl. No.: 650,313

[22] Filed: Feb. 4, 1991

[51] Int. Cl.⁵ ............................................. G01N 21/01
[52] U.S. Cl. ................................ 250/227.21; 385/12; 385/48
[58] Field of Search ................. 250/227.21, 227.14, 250/227.15; 385/12, 13, 39, 47, 48

[56] References Cited

U.S. PATENT DOCUMENTS

| | | | |
|---|---|---|---|
| 1,320,625 | 11/1919 | Kunz. | |
| 2,279,288 | 4/1942 | Orbeck | 101/407 |
| 3,619,030 | 11/1971 | Tomil et al. | 350/96 B |
| 3,619,068 | 11/1971 | Broerman | 356/130 |
| 4,109,997 | 8/1978 | Iverson | 350/23 |
| 4,165,496 | 8/1979 | Di Domenico, Jr. et al. | 385/48 |
| 4,296,995 | 10/1981 | Bickel | 350/96.15 |
| 4,320,291 | 3/1982 | Uramoto | 250/227 |
| 4,325,605 | 4/1982 | Winzer et al. | 350/96.15 |
| 4,398,791 | 8/1983 | Dorsey | 350/96.18 |
| 4,401,360 | 8/1983 | Streckmann et al. | 350/96.18 |
| 4,421,384 | 12/1983 | McMahon | 350/96.29 |
| 4,452,505 | 6/1984 | Gasparian | 350/96.15 |
| 4,459,477 | 7/1984 | Asawa et al. | 250/227 |
| 4,460,242 | 7/1984 | Birch et al. | 350/96.20 |
| 4,462,699 | 7/1984 | Shaw et al. | 374/130 |
| 4,540,237 | 9/1985 | Winzer | 350/96.15 |
| 4,576,436 | 3/1986 | Daniel | 350/96.10 |
| 4,611,884 | 9/1986 | Roberts | 350/96.15 |
| 4,630,255 | 12/1986 | Gouali et al. | 370/3 |
| 4,653,845 | 3/1987 | Tremblay et al. | 350/96.16 |
| 4,653,916 | 3/1987 | Hennig et al. | 356/345 |
| 4,682,844 | 7/1987 | Mori | 350/96.15 |
| 4,688,884 | 8/1987 | Scifres et al. | 350/96.15 |
| 4,690,490 | 9/1987 | Mori | 350/96.15 |
| 4,695,126 | 9/1987 | Cook | 350/96.21 |
| 4,699,511 | 10/1987 | Seaver | 356/136 |
| 4,736,100 | 4/1988 | Vastagh | 250/227 |
| 4,736,360 | 4/1988 | McMahon | 370/3 |
| 4,744,617 | 5/1988 | Hvezda et al. | 350/96.15 |
| 4,778,248 | 10/1988 | Arzur et al. | 250/227.21 |
| 4,850,665 | 7/1989 | Whitehead | 350/96.10 |
| 4,867,520 | 8/1989 | Weidel | 350/96.16 |
| 4,872,739 | 10/1989 | Kahn et al. | 350/96.16 |
| 4,928,004 | 5/1990 | Zimmermann et al. | 250/227.14 |
| 4,950,886 | 8/1990 | Claus et al. | 250/227.14 |
| 4,986,624 | 1/1991 | Sorin et al. | 350/96.19 |

*Primary Examiner*—Carolyn E. Fields
*Attorney, Agent, or Firm*—Charles E. Snee, III

[57] ABSTRACT

An optical fiber connector or coupler (24-54) is provided which partially reflects light travelling in one direction (56) but preferably transmits light without reflection in the opposite direction (58). When such connectors ($C_o$ to $C_n$) are alternated with ambient environment sensors ($S_l$ to $S_n$) in an optical fiber transmission path, light pulses launched in the one direction from a source (60) produce reflected light at a detector (62) which reflected light can be correlated to a preselected characteristic of the environment at each sensor. A series of such connectors can be used without sensors to provide reference signals from points along an optical fiber transmission path. A single fiber path can be used, without the need for a separate fiber for feedback.

28 Claims, 4 Drawing Sheets

METHOD AND APPARATUS FOR SENSING AMBIENT CONDITIONS AT LOCATIONS ALONG AN OPTICAL FIBER TRANSMISSION PATH

CROSS REFERENCE TO RELATED APPLICATION

This application is related to the concurrently filed application Ser. No. 650,312 of Michael A. Marcus for Method and Apparatus for Providing Reference Signals from Points Along an Optical Fiber Transmission Path.

DESCRIPTION

1. Technical Field

The present invention concerns methods and apparatus using optical fibers for sensing ambient conditions or characteristics at a plurality of locations along an optical fiber transmission path. More particularly, this invention relates to such method and apparatus in which such ambient conditions can be measured using an open loop single fiber or bundle of fibers, rather than a closed loop fiber or bundle of fibers as have been in use prior to this invention.

2. Background Art

A variety of connectors, couplers and beam splitters for use with optical fibers have been discribed in the patent literature. For example, U.S. Pat. No. 3,619,030 discloses a pair of optical fiber cables connected with a partial mirror disposed between the connected ends of the cable. The assembly is intended to transmit in one direction from cathode ray tubes images which are uncontaminated by stray images without any reflection. U.S. Pat. No. 4,540,237 discloses a coupler for three optical fibers in which the ends of the fibers are cut at various angles. The coupled fibers are in contact and are said to transmit light with minimal losses. U.S. Pat. No. 4,611,884 discloses an emitter reflectance method of making a bidirectional optical fiber coupler said to have the ability to transmit light in either direction with minimal internal reflection or attenuation. The coupler comprises a molded plastic body containing a beam splitting surface for light transmitted from an optical fiber. U.S. Pat. No. 4,695,126 discloses a coupler in which the ends of the fibers form an acute angle with respect to the longitudinal axes of the fibers and the fibers are positioned at an angle to eliminate back reflection.

Various instruments are also known which comprise optical fibers. U.S. Pat. No. 3,619,068 discloses a refractometer for use in liquid chromatography in which light passes through an optical fiber cable having an end surface at an angle, the surface being in contact with the fluid whose composition is to be measured. U.S. Pat. No. 4,320,291 discloses an instrument for measuring the refractive index of a fluid using external reflectors. U.S. Pat. No. 4,421,384 discloses an optical fiber transducer in which light is reflected back along the fiber from specially angled end faces to provide a measurement of the spacing of the end faces from a nearby block of optical material. U.S. Pat. No. 4,462,699 discloses an optical fiber temperature transducer comprising coatings whose indices of refraction vary with ambient temperature. U.S. Pat. No. 4,699,511 discloses an instrument for measuring index of refraction in which a prism is used to direct light from one fiber end to another, as a function of the index of refraction of the ambient medium.

While devices of the types described in these patents have achieved a certain degree of acceptance in science and industry, a number of persistent problems have gone unsolved. In networks of optical fibers, light signals are launched into a fiber at one location for receipt at another; however, confirming at the one location that the signals have indeed arrived at the other typically has required a return loop of fiber from the other location. Thus, to simplify such networks, it has been desired to able to monitor such receipt of signals without the use of closed loops of fibers. In measurement systems using optical fibers to monitor ambient conditions, the effective use of a plurality of sensors distributed along a single fiber or bundle of fibers has been frustrated by the lack of a reliable technique for producing a reference signal from each sensor location along the fiber, as would be needed to separately detect the response of each of the plurality of sensors. In applications where two or more fibers must be coupled or connected, considerable difficulty has been experienced with reliably, consistently preparing the fiber ends for joining.

SUMMARY OF THE INVENTION

A primary objective of the present invention is to provide a method and apparatus for optically producing reference signals from points along an optical fiber transmission path.

Another primary objective of the present invention is to provide a method and apparatus for optically sensing ambient conditions in the environment along an optical transmission path.

A further objective of the present invention is to provide such a method and apparatus which do not require the use of a return or closed loop of optical fiber.

Still another objective of the present invention is to provide an apparatus for asymmetrically coupling or connecting optical fibers in such a way that light transmitted from a first direction is partially reflected and partially transmitted, while light from an opposite, second direction primarily is transmitted without significant back reflected light toward such second direction.

Yet another objective of this present invention is to provide such a coupling or connecting apparatus in which light transmitted from either direction is partially reflected and partially transmitted.

A still further objective of the invention is to provide a simple, improved method for making such a coupling or connecting apparatus.

Another objective of the invention is to provide such a method and apparatus in which recycling of light signals between successive coupler or connectors is minimized, thus reducing optical signal noise.

These objectives are given only by way of illustrative examples; thus other desirable objectives and advantages inherently achieved by the disclosed invention may occur or become apparent to those skilled in the art. Nonetheless, the scope of the invention is to be limited only by the appended claims.

To facilitate better understanding of the invention, reference is made to FIG. 1 which shows a schematic longitudinal crossection of a typical optical fiber 10. As is understood by those skilled in the art, an optical fiber functions optimally by transmitting light almost solely along its essentially cylindrical core 12 due to total internal reflection of light at the interface between core 12 and the surrounding clad 14. If total internal reflection is not achieved, a potentially unacceptable fraction of the incident light may be lost into clad 14, rather than being transmitted along core 12. In order to ensure total internal reflection, the angle $\Theta$ between a ray of light 16 and a normal 18 to the core/clad interface must be greater than the critical angle for total internal reflection at the interface. For a step index fiber of the type shown, the critical angle can be determined from Snell's law, which provides that $$n_1 \sin \Theta_1 = n_2 \sin \Theta_2$$

where $n_1$ is the index of refraction of the incident medium; $n_2$ is the index of refraction of the medium into which the transmitted light would travel; and $\Theta_1$ and $\Theta_2$ are the angles of incidence and refraction respectively. From the geometry of the core/clad interface illustrated in FIG. 1, it can be shown that the minimum angle $\Theta_{min}$ for transmission of light along core 12 by total internal reflection is given by $$\sin \Theta_{min} = n_2/n_1$$

The numerical aperture NA of fiber 10 is a function of the sine of the maximum acceptance angle $\Theta_c$ for light to transmit along core 12 by total internal reflection and is given by $$NA = n_o \sin \Theta_c$$

where $n_o$ is the index of refraction of the external medium. Consideration of FIG. 1 shows that the maximum angle of refraction with respect to the longitudinal axis of fiber 10 for light entering from the external medium is given by $(90° - \Theta_{min})$. Applying Snell's law to the external medium/core interface yields $$n_o \sin \Theta_c = n_1 \cos \Theta_{min}$$

Calculation yields $$\Theta_c = \arcsin(n_1^2 - n_2^2)^{\frac{1}{2}}/n_o$$

$\Theta_c$ is the external critical angle for light entering the fiber from the external medium of index $n_o$. A truncated cone formed at the entrance face of core 12 with an apex angle $\Theta_c$ defines the maximum acceptance cone of the fiber and substantially all light passing into the core through such a cone will transmit along the core by total internal reflection. The internal critical angle of the fiber is the angle of refraction $\gamma$, shown in FIGS. 1 and 2 for light transmitted into the fiber from the external medium at $\Theta_c$.

Consider now an optical fiber having an angled, substantially planar end face 20 through which light is to be emitted, as illustrated in FIG. 2. The angle $\phi$ is the angle between end face 20 and a normal 22 to the longitudinal axis of the fiber. From the geometry shown in FIG. 2, it can also be shown that angle $\phi$ is equal to the angle between the longitudinal axis of the fiber and a normal 24 to end face 20. Light travelling along core 12 from left to right in FIG. 2 at angle $\phi$ with respect to the longitudinal axis of fiber 10 would strike end face 20 perpendicularly and would reflect back to the left along core 12 at angle $\phi$ with respect to the longitudinal axis by total internal reflection. According to the present invention, the important angle to consider in the geometry of FIG. 2 is the internal critical angle or incident angle of refraction $\gamma$ into core 12, which is given by $(90° - \Theta_{min})$. The internal critical angle $\gamma$ is given by $$\gamma = \arcsin(1 - n_2^2/n_1^2)^{\frac{1}{2}}$$

When angle $\phi$ is greater than the internal critical angle $\gamma$, essentially no light travelling from left to right in FIG. 2 will be reflected back to the left along core 12 by total internal reflection; but in such a case, reflected light will be lost into clad 14. When in accordance with the present invention, angle $\phi$ is less than the internal critical angle $\gamma$, a portion of the light travelling from left to right will be reflected back to the left along core 12 by total internal reflection; and a further portion will pass through end face 20. Thus by appropriate selection of angle $\phi$, one can determine the percentage of light which will be reflected back along core 12 by total internal reflection. While the foregoing analysis is specific to step index fibers, those skilled in the art will appreciate that a similar analysis applies to graded index fibers, for which an internal critical angle $\gamma$ also can be determined by conventional techniques and used to select the angle $\phi$ of the end face of the fiber.

One preferred embodiment of the invention concerns an improved apparatus for measuring a characteristic of the ambient environment at multiple locations. A source of pulsed light and an optical detector are connected to an optical coupler which (a) receives light from the source and passes it to a light transmitting element, preferably an optical fiber, and (b) receives reflected light from the light transmitting element and passes it to the detector. Along an optical transmission path extended from the light transmitting element, a plurality of coupling or joining means, preferably one or the other of the first and second embodiments of the invention described in the preceding paragraph, are alternated with a corresponding plurality of sensor means which transmit light in either direction as a function of a preselected characteristic of the ambient environment. The coupling or joining means function to (a) receive light from a first direction, reflect a first portion of that light back toward such first direction and transmit a second portion of that light toward a second direction; and (b) receive light from such second direction and transmit at least a portion of the light toward such first direction. Light from the last sensor means in the alternating series of coupling or joining means and sensor means is reflected back toward the last sensor means. As a result of this arrangement, the detector receives the reflected light from the coupling or joining means, in addition to the normal backscattered light. The characteristics of this additional reflected light are proportional to the preselected characteristic of the ambient environment along the optical transmission path.

In accordance with one method of the invention, a characteristic of the ambient environment is measured along an optical fiber transmission path. A pulse of light is directed along the path from a first direction. At a plurality of points along the path, a first portion of the light is reflected back along the path by total internal reflection toward the first direction and a second portion is transmitted along the path toward a second direction. After the second portion passes each of the points, its optical characteristics are modified as a function of a preselected characteristic of the ambient environment before the second portion reaches the next point. The light transmitted in the second direction from the last point along the path is not reflected back along the path toward the first direction. The light thus reflected back along the path toward the first direction is detected as proportional to the preselected characteristic of the ambient environment. In accordance with another, similar method of the invention, light is not transmitted in the second direction from the last point along the path.

BRIEF DESCRIPTION OF THE DRAWINGS

The foregoing and other objectives, features and advantages of the invention will be apparent from the following more particular description of the preferred embodiments of the invention, as illustrated in the accompanying drawings.

DESCRIPTION OF THE PREFERRED EMBODIMENTS

Figure 1:
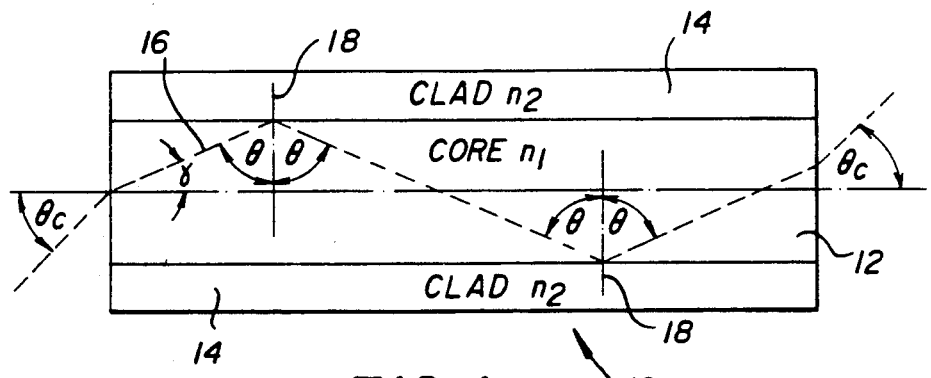
FIG. 1 shows a schematic, longitudinal crossection of an optical fiber.
Figure 2:
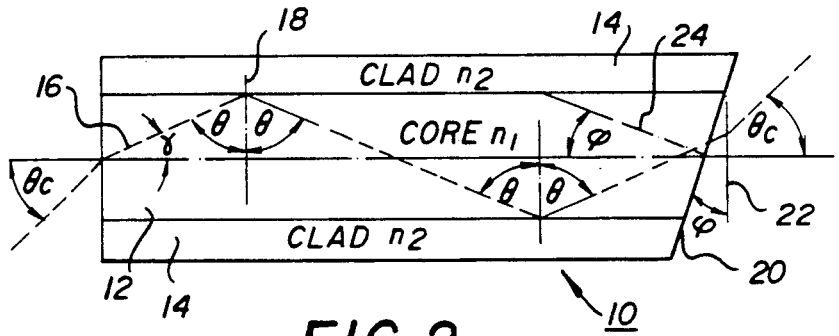
FIG. 2 shows a schematic, longitudinal crossection of an optical fiber having an end face angled in accordance with the invention.

The following is a detailed description of the preferred embodiments of the invention, reference being made to the drawings in which the same reference numerals identify the same elements of structure in each of the several Figures.

Figure 3:
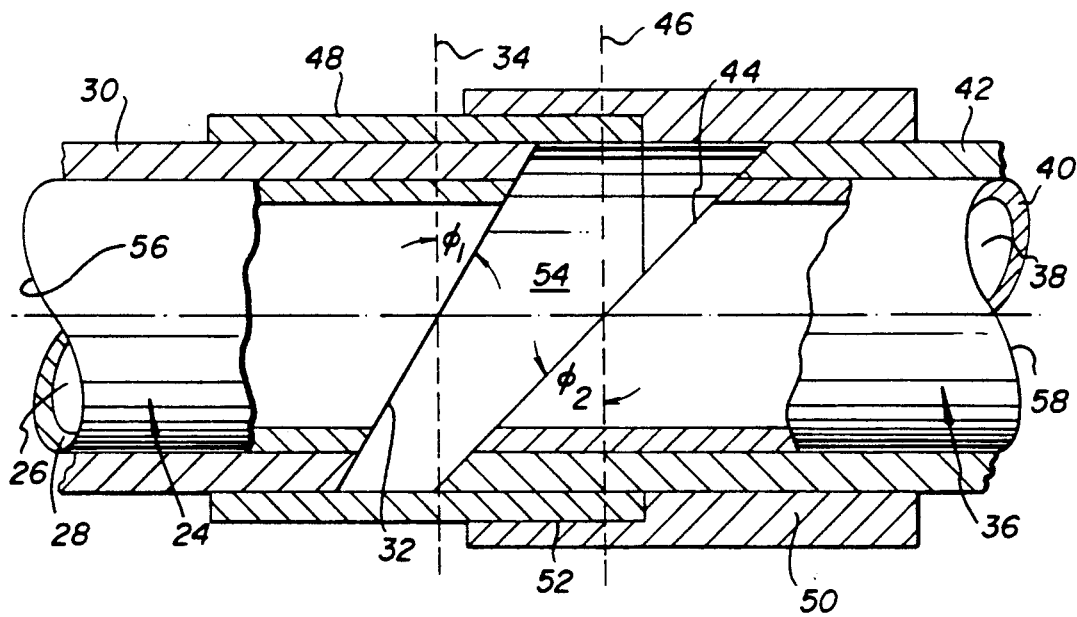
FIG. 3 shows a longitudinal crossection, partially broken away, of an optical connector or coupler according to the invention in which the end surfaces of the optical fibers are spaced from each other and at different angles to the coincident longitudinal axes of the fibers.

FIG. 3 illustrates schematically one embodiment of the optical connector or coupler according to the invention. A first optical fiber 24 comprises in the familiar manner a cylindrical core 26 surrounded by a clad 28 which extends along the length of the fiber. A protective buffer coating or sheath 30, or both, preferably is provided around clad 28 and along the length of the fiber. For ease of illustration and description, the optical fibers shown in the Figures all are single fibers; however, those skilled in the art will appreciate that each embodiment of the invention can be used with both single fibers and groups or bundles of fibers gathered together to form a larger optical fiber transmission path. Thus, unless the context indicates otherwise, the term "fiber" should be read to include such groups or bundles of fibers. The fibers may be of the multimode or single mode variety. The fibers also may be of the same or different diameters on opposite sides of the connector. However, not every fiber in such a bundle need be configured in the manner(s) now to be discussed, so long as at least one pair of input and output fibers is so configured.

Fiber 24 comprises an output end for transmitting light which is formed by an essentially planar end surface 32 extended across core 26 which end surface may also extend across clad 28 and sheath 30. Planar surface 32 is set at an angle $\phi_1$ to a normal 34 to the longitudinal axis of fiber 24. In order to ensure that a portion of the light transmitted through fiber 24 from the left as seen in FIG. 3 is reflected by total internal reflection back toward the left, angle $\phi_1$ is chosen in accordance with the invention to be greater than zero and less than the internal critical angle of fiber 24. This value of angle $\phi_1$ also ensures that a further portion of light from the left will be transmitted through planar surface 32.

A second optical fiber 36 is provided to receive light from fiber 24 and to transmit light back to fiber 24. Fiber 36 comprises a cylindrical core 38 surrounded by a clad 40 which extends along the length of the fiber. A protective buffer coating or sheath 42, or both, preferably is provided around clad 40 and along the length of the fiber. Fiber 36 comprises both an input end for light from fiber 24 and an output end for transmitting light from fiber 36, which input/output end is formed by an essentially planar end surface 44 extended across core 38 which end surface may also extend across clad 40 and sheath 42. Planar surface 44 is set at an angle $\phi_2$ to a normal 46 to the longitudinal axis of fiber 36. Angles $\phi_1$ and $\phi_2$ may be less than, equal to or greater than one another, as required for a given application and as discussed with regard to the remaining embodiments of the invention.

In accordance with the invention, fibers 24,36 are positioned with planar surfaces 32,44 facing each other and with the longitudinal axes of the fibers at an angle which permits at least a portion of the light emanating from the output end of fiber 24 to follow a path within the maximum acceptance cone of fiber 36, and vice versa. The longitudinal axes may be coincident or at an angle to one another. Positioning of the fibers may be achieved with a separable connector comprising a male ferrule half 48 secured to sheath 30 of fiber 24 and a female ferrule half 50 secured to sheath 42 of fiber 36, the two ferrule halves being joined by a threaded joint 52, for example. Of course, if there is no desire to be able to separate the two fibers, ferrule halves 48,50 may be permanently joined as a fixed coupler. Whether ferrules 48,50 form a connector or a coupler, planar surfaces 32,44 are spaced from each other in the illustrated embodiment by a coupling volume 54. Depending on the indexes of refraction of cores 26,38, coupling volume 54 may be filled with a conventional coupling medium which is optically transparent to light transmitted into the volume from either fiber, the index of refraction of the coupling medium preferably being different from that of at least one of cores 26,38. The coupling medium also may have an index of refraction which varies transversely to the longitudinal axis of one or both fibers, if necessary for proper coupling of light between the fibers. In some applications using bundles of fibers, it may be desirable to extend some fibers of the bundle across coupling volume 54 without any break, an arrangement which is considered to be within the scope of the present invention. Either or both of surfaces 32,44 may be coated with conventional materials or provided with fully or partially reflective mirrors, not illustrated, to increase the reflectivity of the surface. Similarly, either or both surfaces may be provided with means such as filters for modifying the optical characteristics of light transmitted through the associated planar surface. Optically active coating materials for surfaces 32,44 could be selected from the group including mirrors, metal oxides, metal fluorides, glass notch filters, band pass filters, polarizing filters and solgels. Polymeric materials could be selected from the group including polyamides, polyimides, gelatin, polymethylmethacrylate and cellulose acetate butyrate. If one or both of surfaces 32,44 is coated with such an optically active material, the indices of refraction of the two cores and the coupling medium could be the same, without departing from the scope of the invention.

In use of the apparatus of FIG. 3, a portion of the light transmitted from the input end 56 of fiber 24 to its output end at planar surface 32 will be reflected by total internal reflection back toward input end 56 and a second portion of such light will be transmitted through planar surface 32 and coupled into the input end of fiber 36 at planar surface 44. When angle $\phi_2$ is greater than the internal critical angle of fiber 36, light transmitted from the output end 58 of fiber 36 to the input end of fiber 36 will be transmitted through planar surface 44 and coupled into the output end of fiber 24; and the portion of light reflected back toward output end 58 will be vanishingly small. When angle $\phi_2$ is less than or equal to the internal critical angle of fiber 36, a portion of light transmitted from output end 58 to the input end of fiber 36 will be reflected by total internal reflection back toward output end 58.

A plurality of couplers or connectors of the type shown in FIG. 3 can be positioned at a correspondingly plurality of points along an optical fiber transmission path. Consider, for example, the system of FIG. 10 without the sensors $S_1$ to $S_n$. If a pulse of light is directed along the path from a first direction, at each of the plurality of points $C_o$ to $C_n$ a first portion of the light will be reflected by total internal reflection back along the path toward the first direction and a second portion of the light will be transmitted along the path toward a second direction. Similarly, at each of the plurality of points, any light traveling from the second direction will be transmitted along the path toward the first direction. Thus, a series of pulses produced by the reflected first portions is directed back along the path to provide signals indicating that light has passed each of the plurality of points and continues along the path past the last point. If the last point is provided with only a reflector, a series of pulses is directed back to indicate that light has reached each point.

Optical fibers can be provided with planar end surfaces 32,34 using simple fixtures and known polishing techniques. For one actual connector of the general type shown in FIG. 3, fibers were clamped into fixtures at small angles with respect to the fiber's longitudinal axis and polished with emery paper until an essentially planar end surface with a smooth finish was obtained. 200/240 μm step index fibers from General Fiber Optics were finished using this process. Planar end surfaces at an 8° angle and a 15° angle were formed on the respective ends of first and second fibers. To position the ends of these fibers as in with the connector or coupler according to this invention, a 0.010 inch (0.0254 cm) diameter hole was drilled in a quartz rod. A 0.020 inch (0.0508 cm) diameter relief hole was drilled at 90° to the axis of the first hole. Norland ultraviolet-curable optical adhesive was placed in the first hole to fill the gap between the two angled fiber ends. The specially polished fibers were inserted into opposite ends of the first hole in the quartz rod so that their planar end surfaces just touched at one edge. The adhesive was then cured using an ultraviolet lamp. When light was passed through the 8° angle side to the 15° angle side, a 3% reflectivity was measured at 820 nm; whereas, in the opposite direction, a less than 0.01% reflectivity was measured. The asymmetric transmission characteristics of the coupler or connector of the invention were clearly demonstrated.

Figure 4:
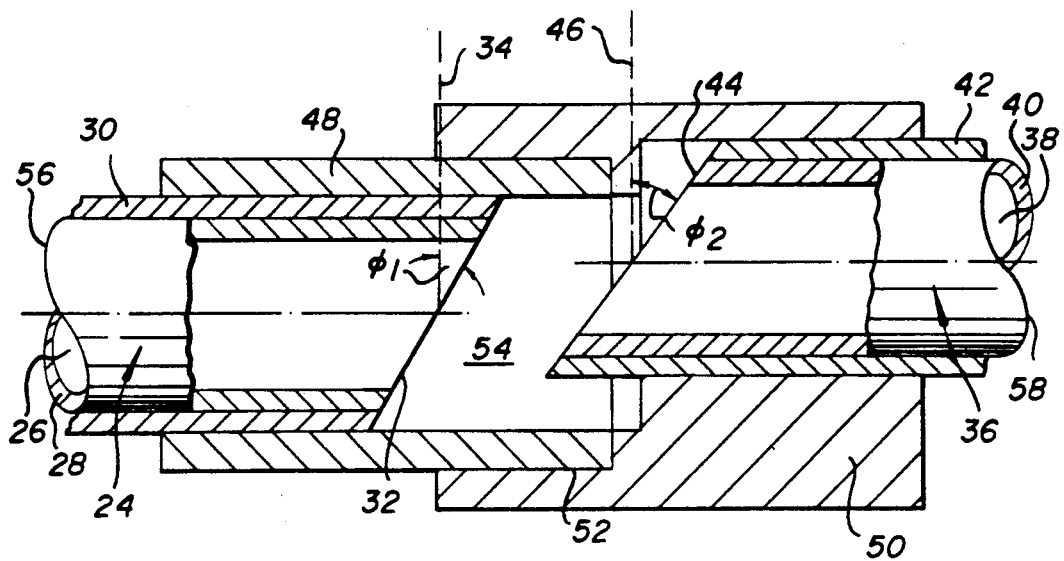
FIG. 4 shows a longitudinal crossection, partially broken away, of an optical connector or coupler according to the invention in which the end surfaces of the optical fibers are spaced from each other and at different angles to the laterally spaced, parallel longitudinal axes of the fiber.
Figure 5:
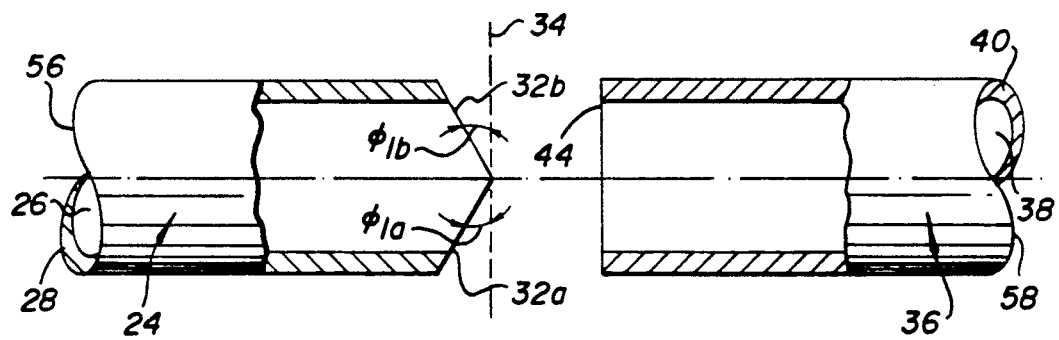
FIG. 5 shows a simplified longitudinal crossection, partially broken away, of an optical connector or coupler according to the invention in which the end surface of one fiber comprises intersecting planar surfaces; and the end surfaces of the two fibers are spaced from each other at different angles to the coincident longitudinal axes of the fibers.
Figure 6:
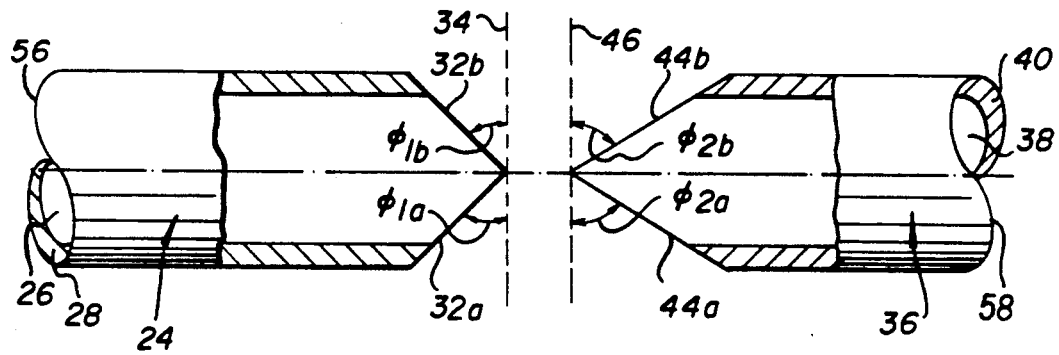
FIG. 6 shows a simplified longitudinal crossection, partially broken away, of an optical connector or coupler according to the invention in which the end surfaces of both fibers comprise intersecting planar surfaces; and the end surfaces of the two fibers are spaced from each other at different angles to the coincident longitudinal axes of the fibers.

FIG. 4 shows a second embodiment of the coupler or connector according to the invention in which the longitudinal axes of the first and second fibers are parallel rather than coincident, but light still will couple across volume 54 from one fiber to the other. It is also within the scope of the invention to place the longitudinal axes at an angle to one another. Otherwise, the embodiment of FIG. 4 is configured and functions in the same manner as that of FIG. 3. FIG. 5 shows only the optical fibers 24,36 of a third embodiment in which fiber 24 is provided with a pair of planar end faces 32a,32b which intersect at the longitudinal axis of the fiber; and fiber 36 is provided with a planar end face 44 which is perpendicular to the longitudinal axis of the fiber. Light reflects back along fiber 24 from both of faces 32a,32b when angles $\phi_{1a}$ and $\phi_{1b}$ are greater than zero but less than the internal critical angle of fiber 24. Surfaces 32a,32b need not intersect at the longitudinal axis of the fiber. FIG. 6 shows only the optical fibers 24,26 of a fourth embodiment in which fiber 24 is provided with end faces 32a,32b which intersect the longitudinal axis of the fiber; and fiber 36 is provided with similar but oppositely facing end faces 44a,44b. Light reflects back along fiber 36 from both faces 44a,44b when angles $\phi_{2a}$ and $\phi_{2b}$ are greater than zero but less than the internal critical angle of fiber 36. Surfaces 44a,44b likewise need not intersect at the longitudinal axis of the fiber.

Figure 7:
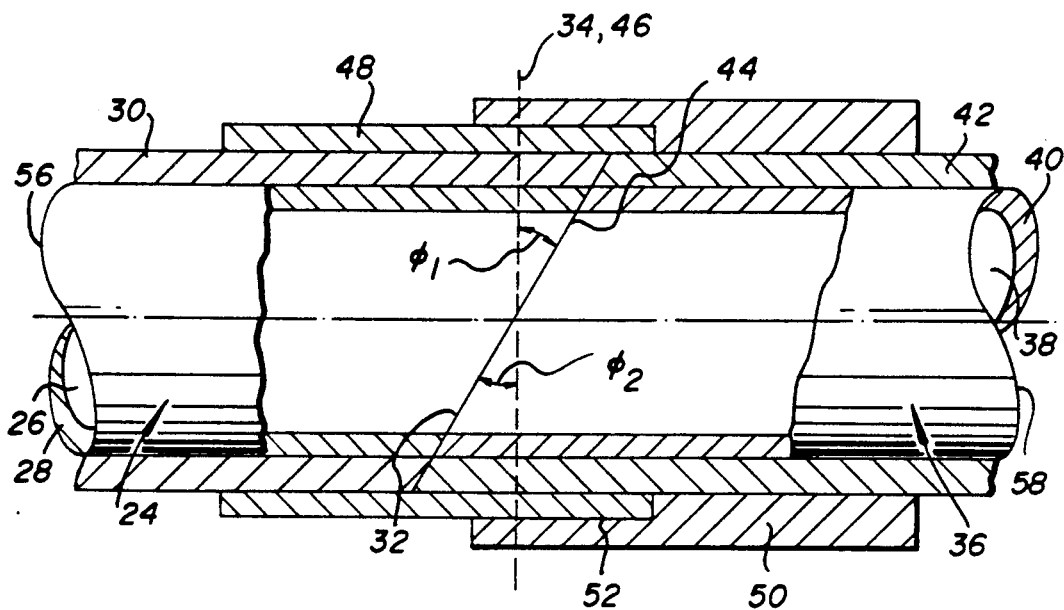
FIG. 7 shows a longitudinal crossection, partially broken away, of an optical connector or coupler according to the invention in which the end surfaces of the fibers essentially are in contact and at the same angle to the longitudinal axes of the fibers.
Figure 8:
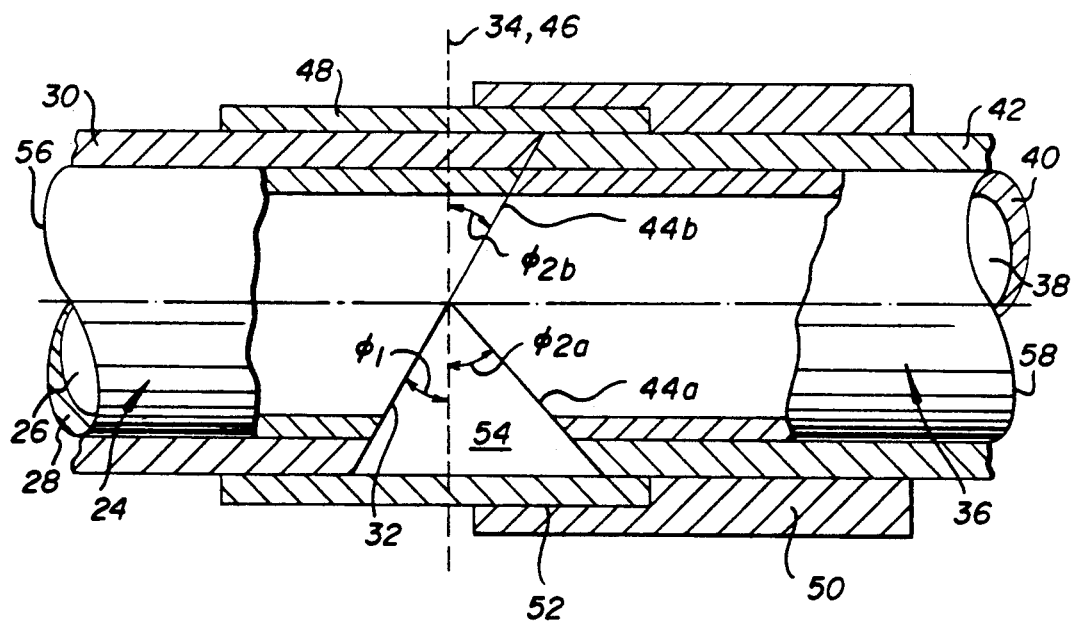
FIG. 8 shows a longitudinal crossection, partially broken away, of an optical connector or coupler according to the invention in which the end surface of one fiber comprises a single planar surface and the end surface of the other fiber comprises intersecting planar surfaces; and the end surfaces of the two fibers are in partial contact with each other and, in part, at different angles to the coincident longitudinal axes of the fibers.
Figure 9:
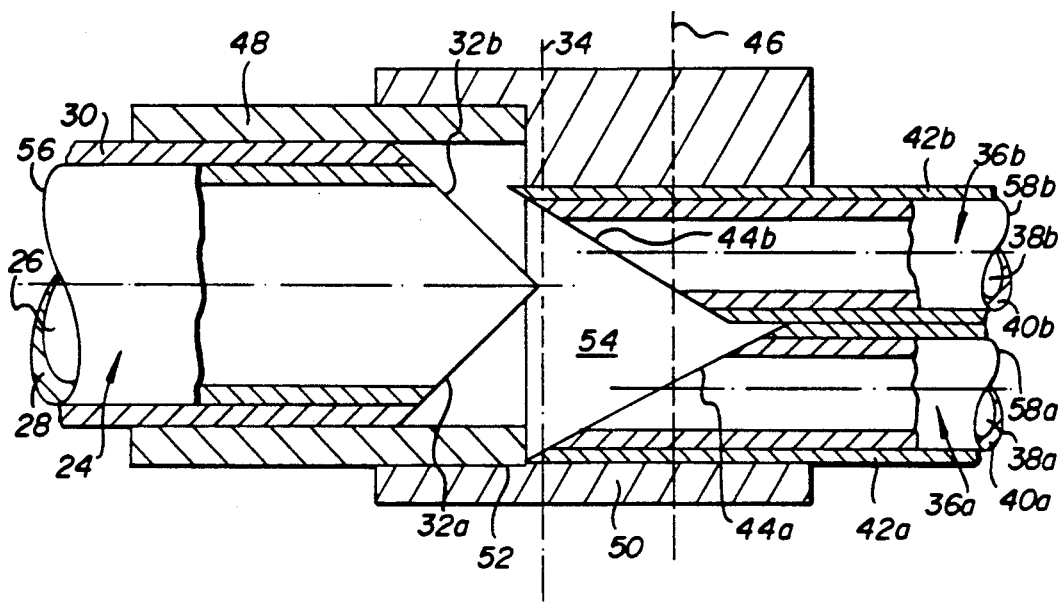
FIG. 9 shows a longitudinal crossection, partially broken away, of an optical connector or coupler according to the invention in which the end surface of one fiber comprises intersecting planar surfaces and the end surfaces of two other fibers comprise single planar surfaces each facing one of the planar surfaces of the one fiber, the end surfaces being spaced from each other at different angles to the laterally spaced, parallel longitudinal axes of the fibers.

FIG. 7 shows a fifth embodiment of the invention in which end surfaces 32,44 are essentially in contact and the indexes of refraction of cores 26,38 are not equal. In the illustrated embodiment, angles $\phi_1$ and $\phi_2$ are equal, making the longitudinal axes of the two fibers coincident; however, it is also within the scope of the invention to make angles $\phi_1$ and $\phi_2$ different and to place the longitudinal axes at an angle to bring the end surfaces 32,44 into essential contact. FIG. 8 shows a sixth embodiment of the invention in which end surface 32 on fiber 24 is in contact only with end surface 44b of fiber 36. The remainder of end surface 32 couples into volume 54. FIG. 9 shows a seventh embodiment of the invention in which end surfaces 32a,32b face and are spaced from end surfaces 44a,44b on second and third fibers 36a,36b and the longitudinal axes are parallel. Thus, the embodiment of FIG. 9 acts as a beam splitter for light from the left and a beam combiner for light from the right.

Figure 10:
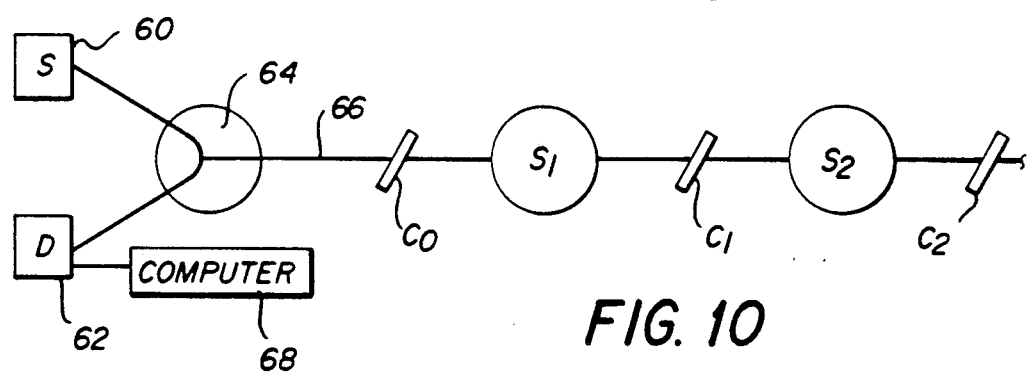
FIG. 10 shows a schematic arrangement of an apparatus according to the invention for measuring characteristics of the environment at multiple locations along an optical fiber transmission path.

The couplers or connectors of FIGS. 3 to 9 find particularly important application in optical systems for measuring a characteristic of the ambient environment at multiple locations along an optical fiber transmission path. It is preferred that angle $\phi_2$ is greater than the internal critical angle of fiber 36, to minimize back reflection. FIG. 10 shows a schematic arrangement for such a system. A conventional source or sources of pulsed light 60 and a conventional optical detector 62, or set of detectors with filters for different wavelengths, are connected to a conventional optical coupler 64 which (a) receives light from source 60 and transmits such light into a light transmitting element 66, such as an optical fiber forming part of an optical fiber transmission path and (b) receives light from element 66 and transmits such light to detector 62. Source 60 may be a narrow wavelength band source such as a laser or a broadband optical source or multiple narrow band optical sources with appropriate filters. The output from detector 62 may be passed to a general purpose computer 68 for time domain analysis in accordance with the analytical technique to be described subsequently. Element 66 transmits light to and from a coupler or connector $C_o$ according to the invention, which transmits light over a length of optical fiber to and from a conventional sensor $S_1$ of a type which transmits light in either direction as a function of a preselected characteristic of the ambient environment.

Sensor $S_1$ could be a fluorescence based sensor, absorbance based sensor or spectroscopic sensor. Examples of the types of characteristics of the ambient environment which are known to affect sensors of this type are humidity, temperature, flow rate, pressure, various chemicals in the ambient, various biological agents and the like. A variety of techniques have been developed for monitoring the concentration of an analyte in a fluid medium based on the effect the analyte has on the optical properties of the medium or based on the response of a sensor exposed to the analyte in the medium. For example, cobalt chloride has been used for decades in indicators of various types which rely on the change in color of the compound in response to changes in ambient humidity. Cobalt bromide, copper chloride, magnesium chloride, nickel chloride, cobalt thiocyanate, barium chloride, cobalt iodide and vanadium chloride, used alone or in various combinations, also have been demonstrated as humidity sensors whose color changes with changes in ambient humidity. Such sensing compounds have been used in combination with various carrier materials such as polymer matrices including sol gels, gelatin, polyvinylpyrrolidone, Nafion polymer and polymethylmethacrylate. Diethyaluminum hydride-2-isoquinoline complexes have also been used as humidity indicators. Rhodamine 6G in a Nafion matrix also has been used as a humidity detector since its absorbance at a wavelength of 520 nm increases with increasing ambient humidity and its fluorescence at 572 nm also changes as a function of humidity. Umbelliferon dye in a matrix of polymethylmethacrylate also has been shown to be sensitive to humidity since its absorbance at 370 nm and fluorescence at 420 nm are functions of humidity in the ambient. Other sensors depend on quenching of fluorescence, such as those using perylenedibutrate and N-substituted derivatives of perylenetetracarboxylic acid bis-imides in appropriate polymer matrices. Porous silicon oxide/titanium oxide and silicon oxide coatings have also been used as humidity sensors. Optic fibers clad with silicon oxide or plasma polymerized hexamethyldisiloxane and ammonia also have been shown to be sensitive to humidity. Various polyimide coatings are also sensitive to moisture in the ambient.

Reagents and other materials also are known whose optical properties change in response to analytes other than moisture. The following are representative of the many examples which can be found in the literature. Oxygen in the ambient can be sensed by perylene dibutyrate dye which, when excited at 450 nm, will produce a green fluorescence at 520 nm, which fluorescence is quenched by oxygen in the ambient. Oxygen can also be sensed by pyresine butryic acid whose fluorescence also is quenched by oxygen in the atmosphere. Oxygen can be detected by 9,10 diphenyl anthracene. Ammonia can be sensed by oxazine perchlorate dye which changes color reversibly in response to ammonia in the ambient. Bromocresol purple changes its absorbance at 580 nm due to the presence of ammonia, shifting from yellow to blue. Ammonia also can be detected by indophenol with casein fluorophase whose fluorescence changes in response to ammonia in the ambient. Glucose can be sensed with fluorescein labelled dextran and concanavillin A on Sepharose. Triphenyl methane dyes change absorbance in the presence of many organic solvents. Similarly, the absorbance of 3,3,diphenylphthalate crystal violet lactone changes in the presence of many organic solvents. Penicillin can be detected by the enzyme penicillinase on glutaraldehyde bound with fluorescein isothiocyanate, since the enzyme binds to penicillin and quenches its fluorescence. Sodium picrate becomes blue in the presence of hydrogen cyanide. Iodine changes from purple to clear in the presence of cyanide ions. Sulphate ions can be sensed using barium chloride which changes from clear to white opaque. Bile acid can be sensed using the reagent 3$\alpha$-hydroxysteriod dehydrogenase together with co-enzyme NAD; since in the presence of the reagent, bile acid converts NAD to NADH which fluoresces at 480 nm upon excitation at 340 nm. Iron can be detected by 1,10 phenanthroline which becomes red as the concentration of iron increases. Aluminum can be detected by pyrocatechol which loses its violet color as the concentration of aluminum increases. Oxazine perchlorate is sensitive to the presence of hydrazine and pyridene. Halides can be detected by acridunium and quinollinium indicators whose fluorescence is quenched by their presence. Chlorine can be sensed by orthocolidine.

Referring again to FIG. 10, sensor $S_1$ transmits light over a length of optical fiber to and from a coupler or connector $C_1$, which transmits light over a length of optical fiber to and from a sensor $S_2$, which transmits light over a length of optical fiber to and from a coupler or connector $C_2$, and so on until the desired number of sensors has been provided to monitor a given area of the environment. As a result of this arrangement, for each pulse of light from source 60, detector 62 receives light reflected back from the several couplers or connectors $C_o$ to $C_n$, in addition to the normal back scattered light observable in optical time domain reflectometry (OTDR). In operation of the distributed sensor system shown in FIG. 10, source 60 emits a short pulse of light at time $T_o$. The speed of light in a medium is inversely proportional to the index of refraction of the medium and it takes light a small but measurable amount of time to travel a given distance. The time between pulses from source 60 should be greater than the time required for light to travel along the entire communication path to connector $C_n$ and reflect back to detector 62. Suppose at time $T_o + T_{Co}$ the light is incident upon connector $C_o$. The reflected portion of the light incident upon connector $C_o$ will then reach detector 62 at time $2(T_o + T_{Co})$. Similarly, if each connector $C_n$ is considered in sequence, the light from connector $C_n$ will reach detector 62 at time $2(T_o + T_{Cn})$. Since sensors $S_1$ to $S_n$ are positioned between the successive connectors $C_n$, the effect of sensor $S_1$ can be determined by taking the intensity ratio of the reflected light pulses at the times of arrival of the reflected pulses from connectors $C_o$ and $C_1$. Similarly, the effect of sensor $S_n$ is found by taking the intensity ratio of the reflected light pulses from connector $C_{n-1}$ to those from connector $C_n$.

In practice, it has been found desirable to use at least two wavelengths of light for sensing. One wavelength should be outside the wavelength band in which the optical properties of sensors $S_1$ to $S_n$ are influenced by the particular characteristic of the environment. This wavelength is used as a reference for determining the percentage of light transmitted through each of the connectors $C_o$ to $C_n$. Another wavelength is used to detect changes in the properties of the sensors due to changes in the environment. In the case of fluorescence based sensors, a third wavelength is used to check for induced fluorescence. It is also within the scope of the invention to combine different sensors along a single optical fiber transmission path. Changes in the reflected pulses during specific time intervals would be related to changes in the environment of the particular sensor being interrogated. A further advantage of this type of distributed sensor system is that crosstalk among the sensors is minimized. Further, when angle $\phi_2$ is greater than the internal critical angle of fiber 36, reflected pulses will not recirculate to create noise in the network.

Figure 11:
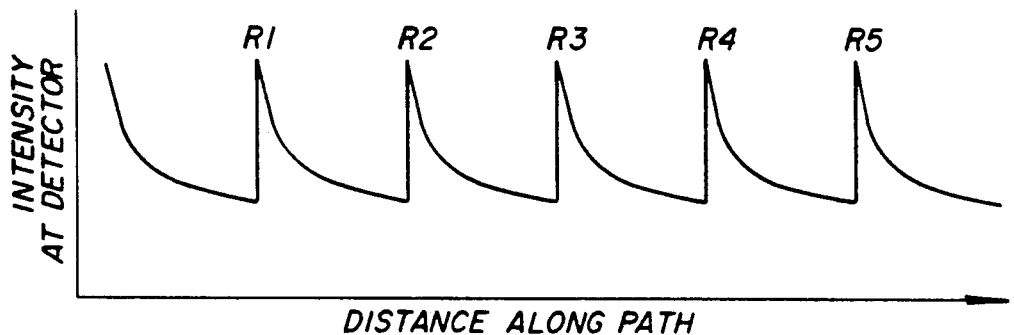
FIG. 11 shows a plot of detector output versus distance from the light source for one embodiment of the apparatus of FIG. 10.

The reflected pulses from the distributed sensor system of FIG. 10 can also be sampled in another manner, independent of the distances of the connectors and sensors from the source of light. In FIG. 10, the connectors $C_o$ to $C_n$ have respective reflectivities $R_o$ to $R_n$, which can be predetermined for various wavelengths. Similarly, the sensors $S_1$ to $S_n$ have respective transmittances $T_1$ to $T_n$, which are dependent on ambient conditions in the environment. Let $P_n$ be the percentage of light transmitted from source 60 which arrives at connector $C_n$, assuming no transmission losses in the sensors. When $R_1 P_1^2 = R_2 P_2^2 = R_n P_n^2$, the signal observed at detector 62 would be the same from each connector $C_n$, assuming no transmission losses in the sensors. In practice, to achieve this condition, the reflectivity of the connectors would have to increase along the transmission path, to account for losses as a function of fiber length and losses in connectors $C_n$. This has been accomplished in laboratory systems of the type shown in FIG. 10 which included two sensors and three connectors. In such a case, the observed ODTR trace would appear as in FIG. 11. Each subsequent local maximum in the trace would be the signal obtained from reflected pulses of light from each subsequent connector. When the sensors are functioning properly, the detected signal for $D_1$ can be shown to be $R_1 T_1^2 P_1^2$; and for $D_2$ the signal would be $R_2 T_2^2 P_2^2 T_1^2$, which by substitution equals $D_1 T_2^2$. Thus, the detected signal $D_n$ for each sensor can be shown to be equal to $(D_{n-1})T_n^2$, thus simplifying calibration of the system. In the case of identical sensors in a uniform environment, the ratio between adjacent sensors would be a constant.

Whatever analytical technique is used to evaluate the output of detector 68, the mode of operation of the embodiment of FIG. 10 is that a pulse of light is directed from source 60 along the path toward connector $C_o$. At a plurality of points $C_o$ to $C_n$ along the path, a first portion of the light is reflected back along the path by total internal reflection toward coupler 64 and a second portion is transmitted along the path toward the next connector. After the second portion passes each connector, its optical characteristics are modified by one of sensors $S_1$ to $S_n$ as a function of a preselected characteristic of the ambient environment before the second portion reaches the next connector. The light transmitted in the second direction from the last connector along the path is not reflected back along the path toward coupler 64; so that, some light continues along the path. The series of pulses of light thus directed back along the path toward coupler is detected as proportional to the preselected characteristic of the ambient environment. In accordance with an alternative mode of operation of the invention, light is not transmitted in the second direction from the last connector along the path but is reflected back toward coupler 64; so that, the path ends at the last connector.

While my invention has been shown and described with reference to particular embodiments thereof, those skilled in the art will understand that other variations in form and detail may be made without departing from the scope and spirit of my invention.

Having thus described my invention in sufficient detail to enable those skilled in the art to make and use it, I claim as new and desire to secure Letters Patent for:

1. Apparatus for measuring one or more characteristics of the ambient environment at multiple locations, comprising:
   a source of pulsed light;
   an optical detector;
   a light transmitting element;
   an optical coupler connected (a) to receive light from said source and transmit such light into said light transmitting element and (b) to receive light from said light transmitting element and transmit such light into said detector;
   a first plurality of elements comprising means for (a) receiving light from a first direction, reflecting a first portion of such light back toward said first direction while transmitting a second portion of such light toward a second direction; and (b) receiving light from said second direction and transmitting at least a portion of such light toward said first direction;

a second plurality of elements comprising sensor means for altering light transmitted toward said first or second direction as a function of a preselected characteristic of the ambient environment, the first member of said first plurality being connected to receive light from said light transmitting member and to transmit light toward said second direction to the first member of said second plurality; the second and each remaining member of said first plurality being connected to receive light from a respective member of said second plurality; and the second and each remaining member of said second plurality being connected to receive light from a respective member of said first plurality, thereby defining an alternating series of means for receiving and means for transmitting, said series ending with the last of said means for transmitting;

means connected for reflecting light from said last means for transmitting back toward said last means for transmitting, whereby said detector receives the light reflected back from said means for receiving and said means for reflecting in addition to back scattered light, the intensity of said reflected light being proportional to said characteristic; and means for comparing the intensity of said reflected light from adjacent pairs of said first plurality and for determining said characteristic at each of said second plurality located between said adjacent pairs, as a function of said comparing of intensity.

2. Apparatus according to claim 1, wherein said means for receiving further reflects back toward said second direction a portion of the light from said second direction.

3. Apparatus according to claim 1, wherein each said means for receiving comprises:

a first optical fiber comprising a first core with a longitudinal axis, said first fiber having an input end for receiving light in said one direction and an output end for transmitting light, said output end comprising at least one planar surface extended at least partially across said first core, there being a first angle between said planar surface and a normal to said axis, the magnitude of said first angle being greater than zero and less than the internal critical angle of said first fiber;

a second optical fiber comprising a second core with a longitudinal axis, said second fiber having an input end for receiving light from said first fiber and an output end for transmitting light in said second direction, said input end of said second fiber comprising at least one further planar surface extended at least partially across said second core, there being a second angle between said further planar surface and a normal to said axis of said second fiber; and means for positioning said first and second fibers with said planar surfaces facing and spaced from one another and with said longitudinal axes at a third angle which permits at least a portion of the light from said first fiber to follow a path within the maximum acceptance cone of said second fiber, and vice versa;

whereby a first portion of light transmitted from said input end of said first fiber to said output end of said first fiber is reflected due to said magnitude of said first angle by total internal reflection back toward said input end of said first fiber and a second portion of light transmitted from said input end of said first fiber is transmitted through said planar surface of said first fiber and is coupled into said second fiber; and at least a portion of light transmitted from said output end of said second fiber to said input end of said second fiber is transmitted through said planar surface of said second fiber and is coupled into said first fiber.

4. Apparatus according to claim 3, wherein said second angle is greater than the internal critical angle of said second fiber.

5. Apparatus according to claim 3, wherein said second angle is less than or equal to the internal critical angle of said second fiber.

6. Apparatus according to claim 3, wherein at least one of said first and second fibers comprises a plurality of smaller fibers each having a core and at least one planar input or output end surface.

7. Apparatus according to claim 3, wherein said longitudinal axes are parallel.

8. Apparatus according to claim 3, wherein said at least one planar surface on either or both of said first and second fibers comprises two intersecting planar surfaces.

9. Apparatus according to claim 3, wherein the space between said facing planar surfaces is filled with a coupling medium which is optically transparent to light transmitted from either of said fibers.

10. Apparatus according to claim 9, wherein said coupling medium has an index of refraction which varies transversely to said longitudinal axis of said first fiber.

11. Apparatus according to claim 9, wherein the index of refraction of said medium is the same as that of said cores, further comprising means located at said at least one planar surface of said first fiber or said second fiber or both, for modifying the optical characteristics of light transmitted through said planar surface of said first or second fiber.

12. Apparatus according to claim 3, further comprising means located at said at least one planar surface of said first fiber or said second fiber or both, for increasing the reflectivity of said planar surface or said first or second fiber.

13. Apparatus according to claim 3, further comprising means located at said at least one planar surface of said first fiber or said second fiber or both, for modifying the optical characteristics of light transmitted through said planar surface of said first or second fiber.

14. Apparatus according to claim 3, wherein said means for positioning comprises means for selectively separating and rejoining said first and second fibers.

15. Apparatus according to claim 3, wherein said first and second angles are different.

16. Apparatus according to claim 1, wherein said means for receiving comprises:

a first optical fiber comprising a first core with a first index of refraction and a longitudinal axis, said first fiber having an input end for receiving light and an output end for transmitting light, said output end comprising at least one planar surface extended at least partially across said first core, there being a first angle between said planar surface and a normal to said axis, the magnitude of said first angle being greater than zero and less than the internal critical angle of said first fiber;

a second optical fiber comprising a second core with a second index of refraction not equal to said first index of refraction and a longitudinal axis, said second fiber having an input end for receiving light from said first fiber and an output end for transmitting light, said input end of said second fiber comprising at least one further planar surface extended at least partially across said second core, there being a second angle between said further planar surface and a normal to said axis of said second fiber; and means for positioning said first and second fibers with said planar surfaces contacting one another with said longitudinal axes at a third angle which permits at least a portion of the light from said first fiber to follow a path within the maximum acceptance cone of said second fiber, and vice versa;

whereby a first portion of light transmitted from said input end of said first fiber to said output end of said first fiber is reflected due to said magnitude of said first angle by total internal reflection back toward said input end of said first fiber and a second portion of light transmitted from said input end of said first fiber is transmitted through said planar surface of said first fiber and is coupled into said second fiber; and at least a portion of light transmitted from said output end of said second fiber to said input end of said second fiber is transmitted through said planar surface of said second fiber and is coupled into said first fiber.

17. Apparatus according to claim 16, wherein said second angle is greater than the internal critical angle of said second fiber.

18. Apparatus according to claim 16, wherein said second angle is less than or equal to the internal critical angle of said second fiber.

19. Apparatus according to claim 16, wherein at least one of said first and second fibers comprises a plurality of smaller fibers each having a core and at least one planar input or output end surface.

20. Apparatus according to claim 16, wherein said longitudinal axes are parallel.

21. Apparatus according to claim 16, wherein said second angle is greater than the internal critical angle of said second fiber.

22. Apparatus according to claim 16, wherein said at least one planar surface on either or both of said first and second fibers comprises two intersecting planar surfaces.

23. Apparatus according to claim 16, further comprising means located at said at least one planar surface of said first fiber or said second fiber or both, for increasing the reflectivity of said planar surface of said first or second fiber.

24. Apparatus according to claim 16, further comprising means located at said at least one planar surface of said first fiber or said second fiber or both, for modifying the optical characteristics of light transmitted through said planar surface of said first or second fiber.

25. Apparatus according to claim 16, wherein said means for positioning comprises means for selectively separating and rejoining said first and second fibers.

26. Apparatus according to claim 16, wherein said first and second angles are different.

27. A method for measuring one or more characteristics of the ambient environment along an optical fiber transmission path, comprising the steps of:

directing a pulse of light along said path from a first direction;

at a plurality of points along said path, reflecting a first portion of said light by total internal reflection back along said path toward said first direction while transmitting a second portion of said light along said path toward a second direction;

after each of said plurality of points, modifying the optical characteristics of said second portion of said light as a function of a preselected characteristic of the ambient environment and then transmitting said second portion along said path;

after modifying said second portion of light transmitted from the last of said points, reflecting at least a portion of said light back along said path toward said first direction;

at each of said plurality of points, transmitting along said path toward said first direction any light travelling along said path from said second direction, whereby light is reflected back along said path to provide signals with an intensity proportional to said preselected characteristic; and comparing the intensity of said reflected light from adjacent pairs of said plurality of points and determining said characteristic of the ambient environment between said adjacent pairs as a function of said comparing of intensity.

28. A method for measuring one or more characteristics of the ambient environment along an optical fiber transmission path, comprising the steps of:

directing a pulse of light along said path from a first direction;

at a plurality of points along said path, reflecting a first portion of said light by total internal reflection back along said path toward said first direction;

at each of said plurality of points except the last one along said path, transmitting a second portion of said light along said path toward a second direction;

after each of said plurality of points except the last one along said path, modifying the optical characteristics of said second portion of said light as a function of a preselected characteristic of the ambient environment and then transmitting said second portion along said path;

after modifying said second portion of light transmitted from the last of said points, reflecting at least a portion of said light back along said path toward said first direction;

at each of said plurality of points except said last one, transmitting toward said first direction any light travelling along said path from said second direction, whereby light is reflected back along said path to provide signals with an intensity proportional to said preselected characteristic along said path; and comparing the intensity of said reflected light from adjacent pairs of said plurality of points and determining said characteristic of the ambient environment between said adjacent pairs as a function of said comparing of intensity.

* * * * *